（12）United States Patent
Denove et al.

(10) Patent No.: US 9,204,874 B2
(45) Date of Patent: *Dec. 8, 2015

(54) SUTURE PASSING K-WIRE

(71) Applicant: Arthrex, Inc., Naples, FL (US)

(72) Inventors: Peter A. Denove, Naples, FL (US); Kris A. DiNucci, Scottsdale, AZ (US); Karen L. Gallen, Naples, FL (US)

(73) Assignee: Arthrex, Inc., Naples, FL (US)

( * ) Notice: Subject to any disclaimer, the term of this patent is extended or adjusted under 35 U.S.C. 154(b) by 357 days.

This patent is subject to a terminal disclaimer.

(21) Appl. No.: 13/848,293

(22) Filed: Mar. 21, 2013

(65) Prior Publication Data

US 2013/0218176 A1   Aug. 22, 2013

Related U.S. Application Data

(63) Continuation of application No. 12/639,734, filed on Dec. 16, 2009, now Pat. No. 8,425,554.

(60) Provisional application No. 61/138,041, filed on Dec. 16, 2008.

(51) Int. Cl.
| A61B 17/08 | (2006.01) |
| A61B 17/04 | (2006.01) |
| A61B 17/06 | (2006.01) |
| A61B 17/68 | (2006.01) |
| A61B 17/84 | (2006.01) |
| A61B 17/56 | (2006.01) |

(52) U.S. Cl.
CPC ....... *A61B 17/0469* (2013.01); *A61B 17/06066* (2013.01); *A61B 17/683* (2013.01); *A61B 17/842* (2013.01); *A61B 17/848* (2013.01); A61B 2017/06019 (2013.01); A61B 2017/565 (2013.01)

(58) Field of Classification Search
CPC ..................... A61B 17/0401; A61B 17/06066; A61B 17/0469; A61B 17/1682; A61B 17/1686; A61B 17/848; A61B 17/0485; A61B 17/86; A61F 2/42; A61F 2/4202; A61F 2/4225; A61F 2/4241; A61F 2/4261; A61F 2/46
See application file for complete search history.

(56) References Cited

U.S. PATENT DOCUMENTS

| 4,409,974 | A | * | 10/1983 | Freedland ........................ 606/60 |
| 4,643,178 | A | * | 2/1987 | Nastari et al. .................... 606/74 |
| 4,799,484 | A | * | 1/1989 | Smith et al. .................... 606/223 |
| 5,055,105 | A | | 10/1991 | Hamlin et al. |
| 5,474,554 | A | | 12/1995 | Ku |
| 5,888,203 | A | * | 3/1999 | Goldberg .................... 623/13.11 |
| 6,716,234 | B2 | | 4/2004 | Grafton et al. |

(Continued)

FOREIGN PATENT DOCUMENTS

DE   10 2004 014 036 A1   3/2004

*Primary Examiner* — Dianne Dornbusch
(74) *Attorney, Agent, or Firm* — Dickstein Shapiro LLP

(57) ABSTRACT

A method and apparatus for bunion repair using a suture passing K-wire configured to easily pass through bone tunnels with suture trailing. The suture passing K-wire includes a tapered guide pin with a multi-diameter shaft (i.e., comprising at least two regions or sections that have different diameters) and a loop which is securely attached to an end of the guide pin (i.e., to the smaller diameter section of the guide pin). The reconstruction system may be formed of a pair of buttons connected by a flexible strand. The procedure offers indirect placement of buttons and a minimally invasive approach.

7 Claims, 6 Drawing Sheets

(56) References Cited

U.S. PATENT DOCUMENTS

| | | | |
|---|---|---|---|
| 6,733,529 B2 * | 5/2004 | Whelan | 623/13.12 |
| 7,235,091 B2 * | 6/2007 | Thornes | 606/232 |
| 7,651,509 B2 * | 1/2010 | Bojarski et al. | 606/139 |
| 7,875,058 B2 * | 1/2011 | Holmes, Jr. | 606/232 |
| 7,901,431 B2 * | 3/2011 | Shurnas | 606/232 |
| 2002/0077631 A1 * | 6/2002 | Lubbers et al. | 606/72 |
| 2003/0236555 A1 * | 12/2003 | Thornes | 606/232 |
| 2004/0092936 A1 * | 5/2004 | Miller et al. | 606/72 |
| 2008/0027485 A1 * | 1/2008 | Jolly et al. | 606/222 |
| 2008/0177302 A1 * | 7/2008 | Shurnas | 606/228 |
| 2008/0195148 A1 | 8/2008 | Cook et al. | |
| 2008/0208252 A1 * | 8/2008 | Holmes | 606/232 |
| 2009/0292312 A1 * | 11/2009 | Tochimura et al. | 606/223 |
| 2010/0114161 A1 * | 5/2010 | Bojarski et al. | 606/223 |
| 2010/0114162 A1 * | 5/2010 | Bojarski et al. | 606/228 |
| 2010/0217315 A1 * | 8/2010 | Jolly et al. | 606/223 |

\* cited by examiner

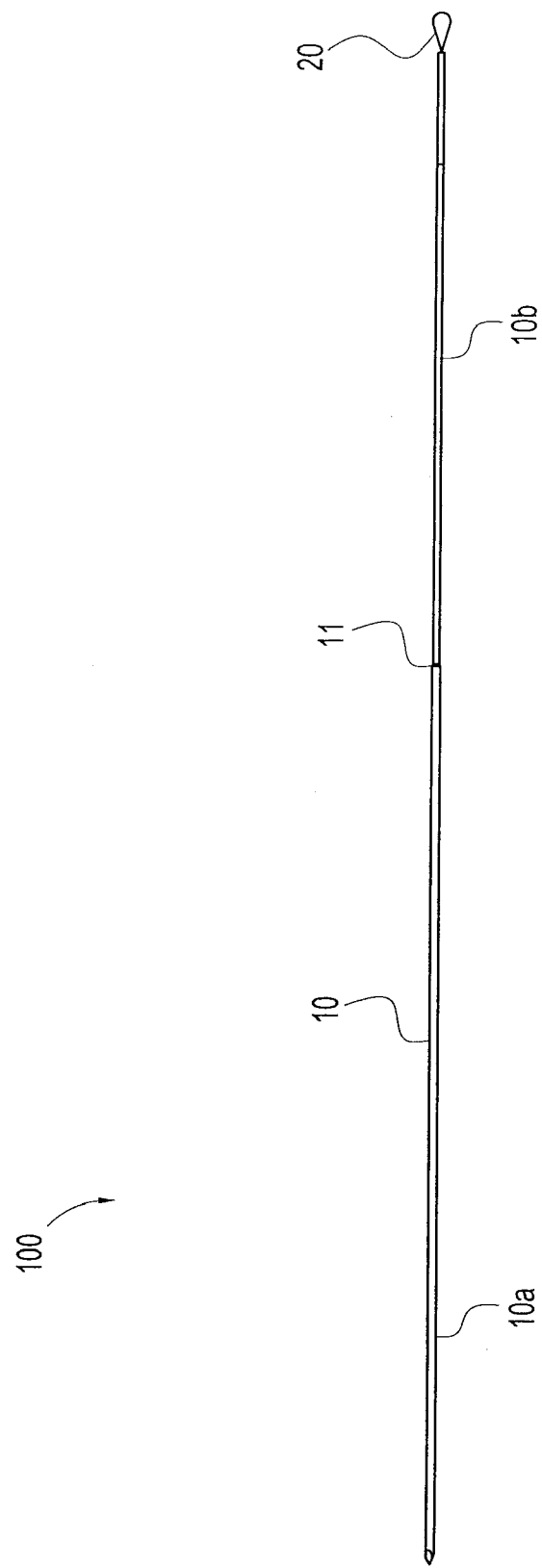

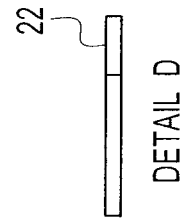
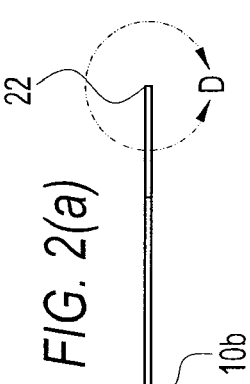
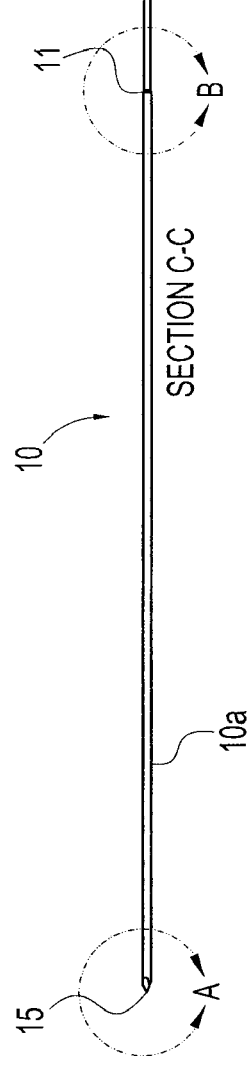
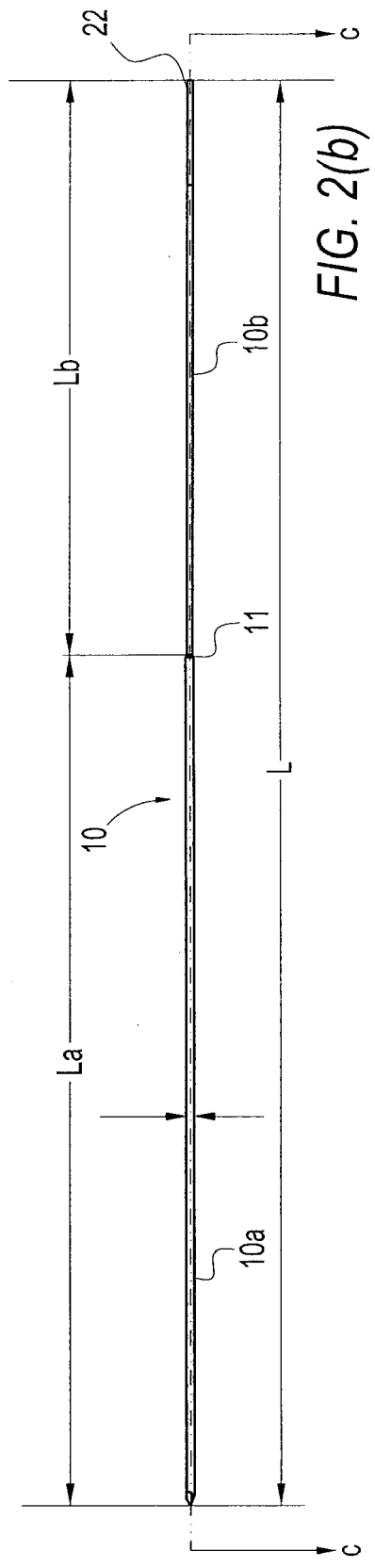

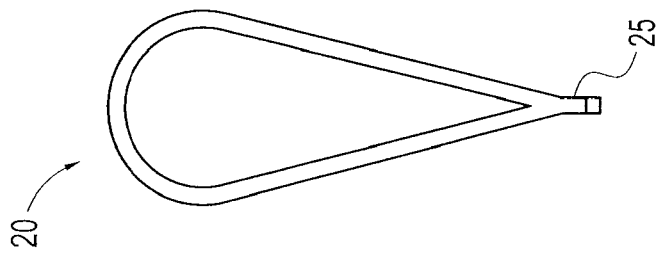

SUTURE PASSING K-WIRE

CROSS-REFERENCE TO RELATED APPLICATIONS

This application is a continuation of U.S. patent application Ser. No. 12/639,734, filed Dec. 16, 2009, now U.S. Pat. No. 8,425,554, issued Apr. 23, 2013, which in turn claims the benefit of U.S. Provisional Application No. 61/138,041, filed Dec. 16, 2008, the entire disclosure of which is incorporated by reference herein.

FIELD OF THE INVENTION

The present invention relates to the field of surgery and, more particularly, to a suture passing K-wire used for small joint and ligament reconstructions.

BACKGROUND OF THE INVENTION

"Hallux valgus" or "hallux abducto valgus" is associated with bunion deformity, where "hallux" refers to the great toe, "valgus" refers to the abnormal slant of the great toe, and "abducto" refers to the abnormal slant or inward leaning of the great toe towards the second toe.

The abnormalities associated with bunion development are caused by a biomechanical abnormality, where certain tendons, ligaments, and supportive structures of the first metatarsal are no longer functioning correctly. This biomechanical abnormality may be due to the structure of the foot—flat feet, excessive ligamentous flexibility, abnormal bone structure—or certain neurological conditions.

The treatment of hallux valgus deformity includes an assessment of the hallux valgus angle, the intermetatarsal angle and the contribution of an interphalageus deformity. Additionally, the presence or absence of arthritic involvement of both the first metatarsocuneiform joint and the first metatarsophalangeal joint are also assessed. The orientation of the distal metatarsal articular angle and the orientation of the first metatarsocuneiform joint are also considered.

Various methods to correct the intermetatarsal angle are known. Soft tissue correction can be achieved by suturing the lateral capsule of the first metatarsal to the medial capsule of the second metatarsal, incorporating the intervening, previously released adductor tendon. A loss of reduction can occur due to the forces that oppose the suture repair as well as the possibility that poor tissue quality can contribute to a loss of reduction.

When more rigid deformities of the intermetatarsal angle are present, it is generally reduced by using a distal or proximal osteotomy of the first metatarsal. Typically, a surgeon cuts into the foot near the bunion, and removes the excess growth of bone with a bone saw. Depending on the degree of deformity, the surgeon may need to cut into the bone of the great toe and realign the bones so that the great toe no longer slants to the outside. Improving the angle of the great toe and repairing the metatarsal bones may require a fastening means to hold them in place. The incisions are later closed with stitches, and a bandage is applied.

Such osteotomies can be technically challenging and difficult to perform. Further, the consequences and potential complications from such surgical procedures is a daunting list that includes delayed union, malunion, nonunion, excessive shortening of the first metatarsal, avascular necrosis, hardware failure and prolonged protected ambulation.

There is a need for a bunion repair technique that is simple, flexible and is performed by a minimally invasive lateral approach, with indirect placement of buttons across the first and second metatarsal. Also needed is a suture passing Kirschner wire (K-wire) that is configured to pass small suture between one or two bones without "binding" the suture in the bone tunnel.

SUMMARY OF THE INVENTION

The present invention overcomes the disadvantages of the prior art and fulfills the needs noted above by providing a surgical procedure for bunion repair using a suture passing K-wire configured to easily pass through bone tunnels with suture trailing. The suture passing K-wire includes a guide pin with a multi-diameter shaft (i.e., comprising at least two regions or sections that have different diameters) and a loop which is securely attached to an end of the guide pin (preferably to the smaller diameter section of the guide pin). The reconstruction system may be formed of a pair of buttons connected by a flexible strand. The procedure offers indirect placement of buttons and a minimally invasive approach. The multi-diameter shaft with the K-wire tip allows drilling directly into bone while small suture can be passed between one or multiple bones without "binding" suture into bone tunnels. The procedure also allows passage of the suture in the same step as drilling (for example, passage of the suture when drilling lateral to medial, from the second metatarsal to the first metatarsal).

These and other features and advantages of the present invention will become apparent from the following description of the invention that is provided in connection with the accompanying drawings and illustrated embodiments of the invention.

BRIEF DESCRIPTION OF THE DRAWINGS

FIG. 1 illustrates a side view of a suture passing K-wire of the present invention;

FIG. 2(a) illustrates a side view of the guide pin (the shaft) of the suture passing K-wire of FIG. 1;

FIG. 2(b) illustrates a cross-sectional view of the guide pin (the shaft) of FIG. 2(a) taken along line C-C of FIG. 2(a);

FIG. 2(c) illustrates an enlarged view of the detail A (trocar tip) of the guide pin (the shaft) of FIG. 2(a);

FIG. 2(d) illustrates an enlarged view of the detail B of the guide pin (the shaft) of FIG. 2(a);

FIG. 2(e) illustrates an enlarged view of the detail D of the guide pin (the shaft) of FIG. 2(a);

FIG. 3(a) illustrates the suture loop of the suture passing K-wire of FIG. 1, prior to assembling the suture loop to the guide pin;

FIG. 3(b) illustrates the suture loop of the suture passing K-wire of FIG. 1, subsequent to assembling the suture loop to the guide pin.

DETAILED DESCRIPTION OF THE PREFERRED EMBODIMENTS

Figure 4:
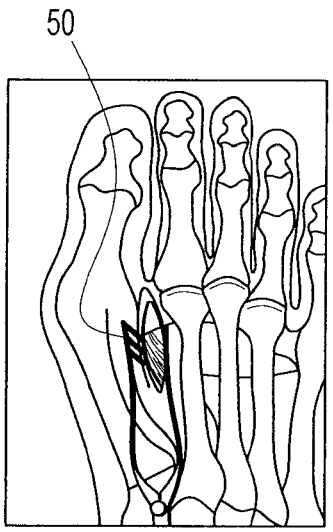
FIGS. 4-12 illustrate subsequent steps of an exemplary method of bunion repair using the suture passing K-wire of FIG. 1.

The present invention provides methods and apparatus for bunion repair. The present invention utilizes a suture passing K-wire for passing a flexible strand attached to a reconstruction system (for example, a suture-button construct) that is placed across the first and second metatarsals. The suture passing K-wire of the present invention is configured to easily pass through bone tunnels with suture trailing.

The suture passing K-wire includes a guide pin with a multi-diameter shaft (i.e., comprising at least two regions or sections that have different diameters) and a loop (for example, a nitinol loop) which is securely attached to an end of the guide pin (preferably to the smaller diameter section of the guide pin). The reconstruction system may be formed of a pair of buttons connected by a flexible strand. The procedure offers indirect placement of buttons and a minimally invasive approach.

The suture passing K-wire is also provided with a sharp tip (trocar tip) so that the K-wire can drill directly into bone while small suture is passed between one or multiple bones without "binding" suture into bone tunnels. The procedure also allows passage of the suture in the same step as drilling (for example, passage of the suture when drilling lateral to medial, from the second metatarsal to the first metatarsal).

According to an exemplary embodiment, the suture passing K-wire of the present invention has a decreased diameter along the shaft of the wire, to ease passage of the suture through small bone tunnels. Once the thicker region of the suture passing K-wire has exited the bones, the smaller diameter section can easily pass through both bone tunnels with suture trailing.

The suture passing K-wire may be employed with a reconstruction system such as a suture-button construct formed of a pair of buttons connected by at least one flexible strand (for example, at least one suture strand). The buttons may have various shapes and configurations, and may be provided with various apertures (in different numbers and with different configurations), to allow the passage of the at least one flexible strand. For example, the reconstruction system may include a first button which may be round and which may include a first set of apertures, and a second button which may be oblong and which may include a second set of apertures (which may be similar to, or different from, the first set of apertures). The buttons may be formed, for example, of titanium, stainless steel, PolyEtherEther-Ketone (PEEK) or Poly-L Lactic Acid (PLLA). If the flexible strand is suture, the suture strand may be FiberWire® suture strand, sold by Arthrex, Inc. of Naples, Fla. Details of reconstructions systems (suture button constructs) which may be employed in the methods of the present invention are set forth in U.S. application Ser. No. 12/016,129, filed on Jan. 17, 2008 (U.S. Application Publ. No. 2008/0208252), the disclosure of which is incorporated in its entirety herewith.

Referring now to the drawings where like elements are designated by like reference numerals, FIGS. 1-3 illustrate a suture passing K-wire 100 formed according to an exemplary embodiment of the present invention. FIGS. 4-12 illustrate a surgical method for repairing bunions using the suture passing K-wire 100 of FIGS. 1-3.

As illustrated in FIGS. 1-3, suture passing K-wire 100 includes a guide pin 10 having a multi-diameter shaft, i.e., a shaft comprising at least two regions or sections that have different diameters. For example, first or distal region 10a has a first diameter (of about 1.1 mm) that is greater than a second diameter of second or proximal region 10b (of about 0.75 mm). Connecting region 11 (shown in more detail in FIG. 2(d)) couples the first and second regions 10a, 10b. In an exemplary embodiment only, connecting region 11 has a tapered diameter (i.e., gradually decreasing from the first diameter of distal region 10a to the second diameter of the proximal region 10b).

Preferably, the guide pin of K-wire 100 is formed of stainless steel or other metals or alloys known in the art. The first or distal region 10a terminates in a sharp tip (trocar tip) 15 which may also be formed of stainless steel. In an exemplary embodiment, the length L of the guide pin 10 is about 180-200 mm, more preferably of about 190 mm, with first region 10a having a length La (FIG. 2(b)) of about 110 mm and second region 10b having a length Lb (FIG. 2(b)) of about 80 mm.

A loop 20 (for example, a Nitinol loop 20) is securely attached to an end of the guide pin 10. FIG. 1 shows loop 20 attached to the smaller diameter section 10b of the guide pin 10, securely fitted within cutout section 22 of the shaft or guide pin 10 (as shown in detail in FIG. 2(e), for example). Loop 20 may be attached to cutout section 22 of the proximal shaft region 10b by various methods known in the art such as crimping, for example. FIGS. 3(a) and 3(b) illustrate the loop 20 before and after assembling to the cutout section 22. Preferably, the diameter of the wire 20 is of about 0.25 mm, so that when the ends 24 of the wire are brought together to form the loop, the combined end region 25 has a diameter about equal to the diameter of the cutout section 22 of the guide pin (i.e., of about 0.5 mm) to allow secure engagement of the loop to the guide pin.

By providing the suture passing K-wire 100 of the present invention with a decreased diameter along the shaft of the wire, the passage of the suture through small bone tunnels is eased. In this manner, once the thicker region 10a of the suture passing K-wire 100 has exited the bones, the smaller diameter section 10b can easily pass through one or both bone tunnels with suture trailing.

FIGS. 4-12 illustrate an exemplary surgical method for repairing bunions using the suture passing K-wire 100 of FIGS. 1-3 employed in conjunction with a reconstruction system 200 that includes a pair of buttons connected by a flexible strand (an exemplary Mini TightRope®, sold by Arthrex, Inc.). Suture passing K-wire 100 of the present invention may be employed, however, with any reconstruction system including, for example, a button with a flexible strand attached therein, or any number of buttons with corresponding flexible strands, or with a suture anchor-button construct (that comprises a fully threaded suture anchor connected by suture extending therefrom to a round button, which is preferably a cup-shaped button). Suture passing K-wire 100 of the present invention may be employed not only for bunion repairs (as detailed below and used in conjunction with a special suture-button construct) but also for passing a flexible strand (such as suture) or a plurality of flexible strands through any bone tunnels or bone openings (or through tunnels formed in adjacent bones or bone segments).

As shown in FIG. 4 (for the distal approach), the first interspace release is first preformed through an incision 50 made between the distal first and second metatarsals. A dorsal medial or medial incision can also be used with appropriate distraction of soft tissues.

Figure 5:
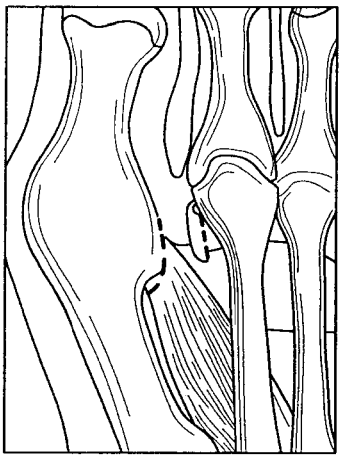

To realign the fibular sesamoid, the adductor tendon is detached from both the base of the proximal phalanx and the fibular sesamoid (FIG. 5). The deep intermetatarsal ligament and lateral capsule are released. Any sesamoid adhesions to the intermetatarsal ligament are also released. The reduction of the IM angle following complete soft tissue release is manually tested.

Figure 6:
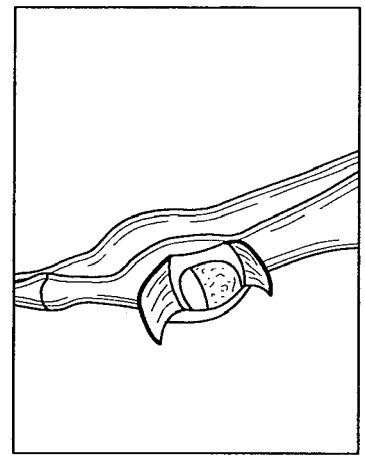

FIG. 6 shows the incision of the medial capsule, exposing the entire medial eminence. The medial eminence is removed, preserving the sesamoid groove on the plantar aspect of the 1st metatarsal.

Figure 7:
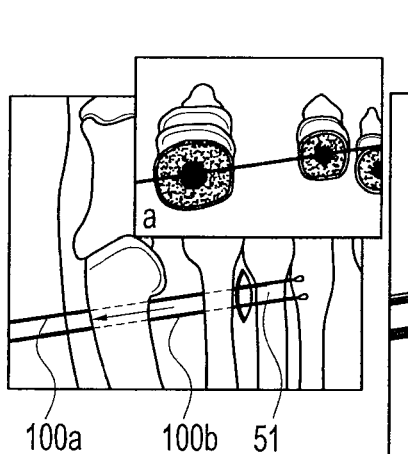

Reference is now made to FIG. 7. The lateral second metatarsal is exposed at site 51 for placement of a reconstruction system (for example, a suture button construct 150 such as the Mini TightRope®150, as shown in FIG. 9(a)). As noted above, details of suture button constructs which may be employed in the methods of the present invention are set forth in U.S. application Ser. No. 12/016,129, filed on Jan. 17, 2008 (U.S. Application Publ. No. 2008/0208252). As detailed in U.S. Application Publ. No. 2008/0208252, suture button construct 150 may comprise first and second buttons with first and second pluralities of apertures that facilitate engagement of a flexible strand (for example, a suture strand) threaded therein. In an exemplary embodiment, the first button has a round configuration (with four circular apertures) and the second button has an oblong configuration (with two triangular apertures). The buttons may also have similar configurations, depending on the characteristics of the anatomical site and structures undergoing repair. For simplicity, the buttons of the suture button construct 150 (the Mini TightRope® 150) of the present invention will be referred to as buttons 155; however, it must be understood that these buttons may have different configurations and geometries. The flexible strand may be formed of suture, for example a high strength suture material such as FiberWire® suture, sold by Arthrex, Inc. of Naples, Fla., and described in U.S. Pat. No. 6,716,234, the disclosure of which is incorporated by reference herein. The FiberWire® suture is formed of an advanced, high-strength fiber material, namely ultrahigh molecular weight polyethylene (UHMWPE), sold under the tradenames Spectra® (Honeywell) and Dyneema® (DSM), braided with at least one other fiber, natural or synthetic, to form lengths of suture material. The suture may optionally include filaments of various colors.

Referring back to FIG. 7, the first metatarsal is reduced with provisional fixation to the second metatarsal. A C-arm is used to assure proper placement of a 1.1 mm tapered suture passing K-wire 100a of the present invention, at the center of the second metatarsal shaft, about 2-3 mm proximal to the neck of the second metatarsal. The second metatarsal is elevated and exposed with an elevator and a small rake retractor (soft tissue) prior to K-wire insertion. The K-wires 100a, 100b (FIG. 7) are placed from the second metatarsal through the first metatarsal and inserted (drilled into the bone) with the thicker region 10a first, followed by the trailing, narrower diameter region 10b with attached loops 20. The wires 100a, 100b exit just proximal to the excised medial eminence, approximately 5 mm apart. Preferably, the suture passing K-wires 100a, 100b are placed simultaneously.

Figure 8:
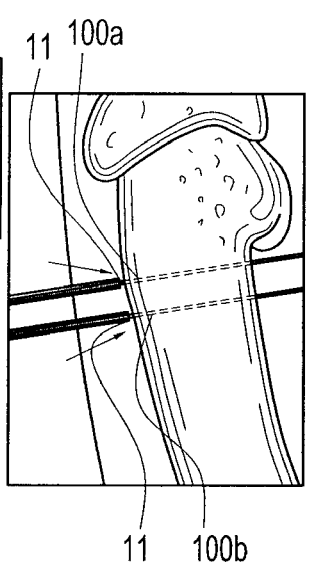

Reference is now made to FIG. 8. With the first metatarsal manually reduced, the K-wires 100a, 100b are positioned so that the tapered portions just exit the medial cortex of the first metatarsal. This will allow easy passage of the #2 FiberWire® through the drilled holes.

Figure 9:
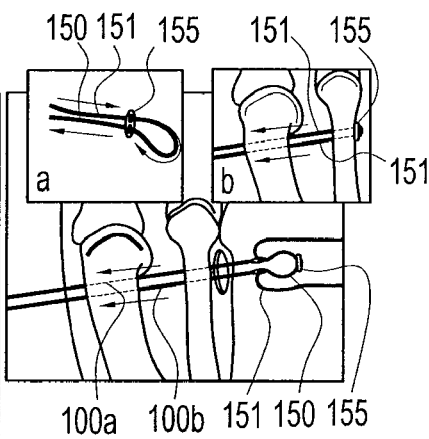

FIG. 9 illustrates the distal construct 150 consisting of an exemplary flexible strand 151 threaded through a button 155 (for example, a #2 FiberWire® strand 151 with two free #2 FiberWire® ends threaded through an oblong button 155, as shown in FIG. 9(a)). One free end of the #2 FiberWire® 151 is inserted through each of the exposed Nitinol wire loops 20 on the lateral side of the second metatarsal. The suture passing K-wires 100a, 100b are pulled medially, passing the free ends through the 1.1 mm pilot holes, as shown in FIG. 9(b).

Figure 9C:
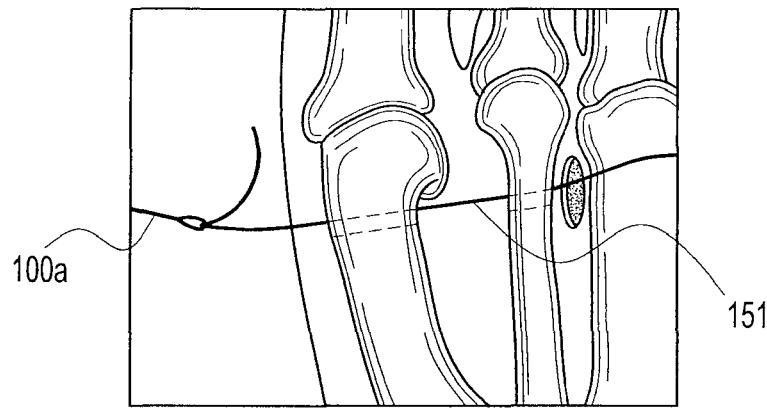
Figure 9D:
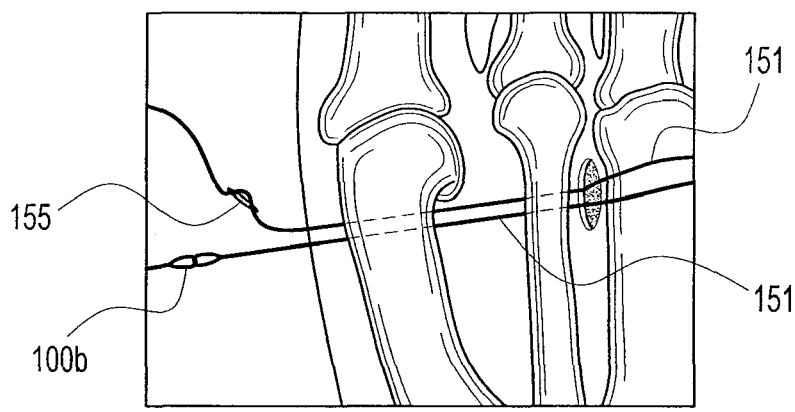
Figure 9E:
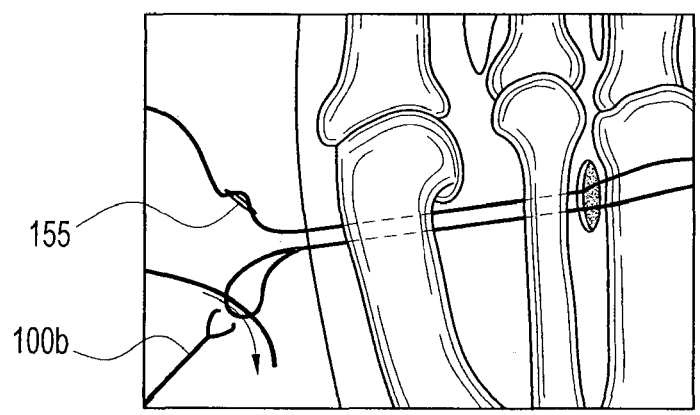

The technique described above positions the suture knots on the medial first metatarsal. Alternatively, the knots may be also placed lateral to the second metatarsal, as shown in FIGS. 9(c)-(e) and with reference to the following steps: One limb of suture 151 is passed through the distal hole 20 using the suture passing K-wire 100a (FIG. 9(c)). The free end of #2 suture 151 is threaded through both holes of the button 155 (FIG. 9(d)). Using a second suture passing K-wire 100b, an accessory strand of 2-0 FiberWire® (formed as a loop) is pulled through the proximal hole (FIG. 9(d)). The 2-0 FiberWire® loop acts as a suture shuttle, pulling the #2 suture from medial to lateral. As shown in FIG. 9(e), the nitinol loop portion of the passing wire is cut. The #2 FiberWire® strand (about 1") is passed through the 2-0 FiberWire® loop and pulled laterally. The construct can now be completed with a button and three knots lateral to the second metatarsal.

Figure 10:
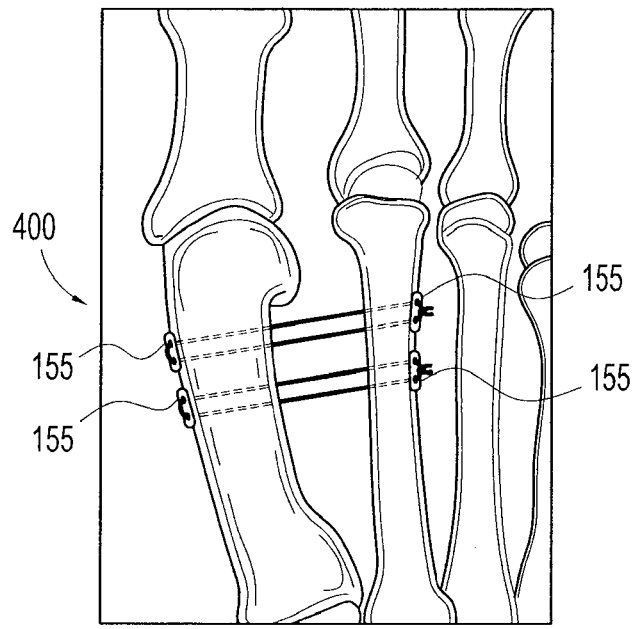

Reference is now made to FIG. 10. After the suture has been passed from lateral to medial, one end of the #2 FiberWire® is rethreaded through opposite holes in the oblong button. If round buttons are used, the buttons are threaded in the same way using opposite holes (see FIG. 11). The first of the two reconstruction systems 150 (the two Mini TightRope® constructs 150) is tied down with one knot, while the second construct 150 is placed about 5-7 mm proximal from the first construct 150. The drilling instructions are repeated (as described above) to place the second construct 150. The surgeon should check the IM angular correction on C-arm prior to final tightening, using three knots for closure.

Figure 11:
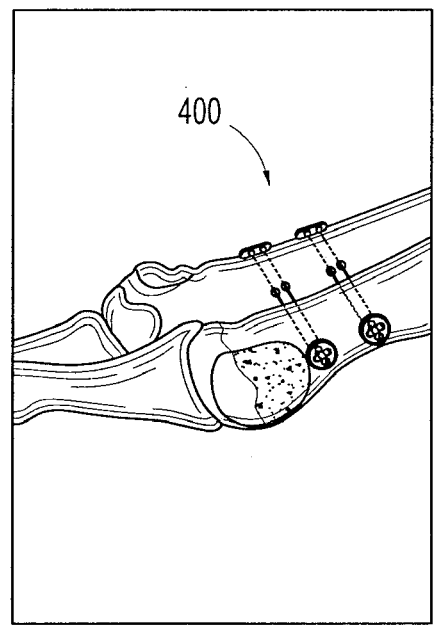
Figure 12:
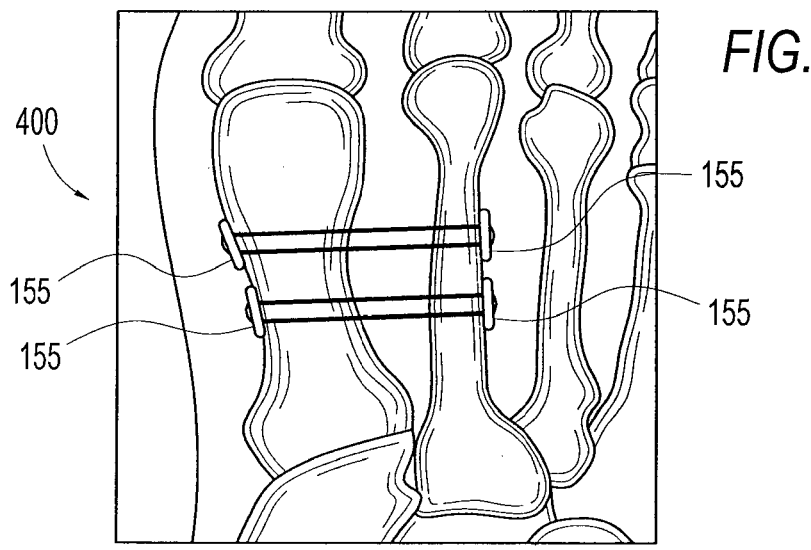

A final, double construct 400 completed using a disposables kit with four round buttons is shown in FIG. 11. FIG. 12 illustrates another view of a final, double construct 400 formed according to a method of the present invention.

A disposable kit 300 of the present invention may comprise, for example, four buttons (for example, four round buttons or four oblong buttons, or two round and two oblong buttons), FiberWire® suture, four 1.1 mm suture passing K-wires and suture passing K-wire (about 8" long). The kit may also comprise a skin marking pen and ruler, and may be employed in conjunction with various accessories (such as, for example, 2.0 FiberWire® (about 38 inches) and FiberWire® scissors, among others.

Hallux Valgus Post-op Protocol
Surgery & Post-op Day 1-4
Posterior fiberglass splint
Heel weight-bearing only
Post-op Day 4-28 (4 weeks)
Heel weight-bearing only
Pneumatic walking boot/Cam walker
Darco bunion splint to maintain position of great toe
Post-op Day 28 (4 weeks-6 weeks)
Possible start in athletic shoe; only lateral or heel weight-bearing
Post-op Day 42 (6 weeks)
Weight-bear through great toe
Recovery depends on soft tissues scarring to hold correction and unload the device. If premature weight-bearing through medial forefoot is initiated, the second metatarsal responds similarly to a stress fracture with long-term edema and mild pain.

The surgical method can also optionally be performed in the opposite direction as that described above, such that the first button ends up on the lateral side of the second metatarsal.

In yet another embodiment of the present invention, the suture passing K-wire of the present invention may be used with a suture anchor-button construct for bunion repair. In an exemplary embodiment only, the suture anchor-button construct comprises a fully threaded suture anchor connected by suture extending therefrom to a round button, which is preferably a cup-shaped button. The suture anchor is inserted through a preformed hole formed in the first metatarsal and into a smaller diameter preformed hole in the second metatarsal, which it is screwed into place. After the first metatarsal and the second metatarsal are pushed together to correct the intermetatarsal angular deformity, the button is advanced upon against the medial surface of the first metatarsal, with the cup of the button in the hole, and secured in place by the tying the suture strands passing through the button.

Although suture passing K-wire 100 of the present invention has been detailed above in conjunction with bunion repairs (and in conjunction with a special suture-button construct), the invention is not limited to this exemplary embodiment. Thus, suture passing K-wire 100 of the present invention may be employed for passing a flexible strand (such as suture) or a plurality of flexible strands through any bone tunnels or bone openings (or through tunnels formed in adjacent bones or bone segments).

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all fall within the scope of the invention. Accordingly, the invention is not to be considered as limited by the foregoing description.

What is claimed as new and desired to be protected by Letters Patent of the United States is:

1. A method comprising:
    inserting a suture passing K-wire from a second bone of a small joint to a first bone of the small joint, the suture passing K-wire comprising a tapered guide pin having a first region with a first diameter and terminating in a sharp tip, and a second region with a second diameter and terminating in an eyelet, the second diameter being smaller than the first diameter, the K-wire being inserted so that the distal end of the second region is adjacent a cortex of the first bone and the eyelet is adjacent a cortex of the second bone;
    passing a flexible strand of a suture-button construct through the eyelet of the K-wire; and
    pulling the K-wire with the flexible strand from the second bone to the first bone so that the K-wire exits the first bone, the flexible strand extends between the first bone and the second bone, and the button is engaged against the second bone;
    forming two pilot holes through the first bone and the second bone;
    passing the flexible strand through a first plurality of apertures of a first button of the suture-button construct so that both free ends of the flexible strand are free;
    inserting each of the free ends of the flexible strand through corresponding eyelets of two tapered K-wires; and
    pulling the two tapered K-wires medially, so that the free ends of the flexible strand are passed through the pilot holes.

2. The method of claim 1, wherein the two K-wires are pulled simultaneously.

3. The method of claim 1, further comprising:
    rethreading one of the free ends of the flexible strand through a second plurality of apertures of a second button; and
    securing the first button on the second bone and securing the second button on the first bone.

4. The method of claim 3, wherein the first button is oblong-shaped having at least two apertures, the apertures being substantially triangular in shape, and the second button is round-shaped having at least four apertures, the four apertures being substantially circular-shaped.

5. The method of claim 3, wherein the flexible strand is formed of a suture comprising a plurality of fibers of ultrahigh molecular weight polyethylene.

6. The method of claim 3, wherein the first bone is the first metatarsal and the second bone is the second metatarsal, and the method further comprises the initial step of making a longitudinal incision over a medial aspect of a first metatarsophalangeal joint to expose a medial eminence; and removing the medial eminence.

7. The method of claim 3, performed in an opposite manner, such that the second button is advanced in an opposite direction through the pilot holes and ends up against a lateral side of the second bone and the first button ends up against the first bone.

* * * * *